US00PP25602P3

(12) United States Plant Patent
Noort

(10) Patent No.: US PP25,602 P3
(45) Date of Patent: May 26, 2015

(54) ***ECHINACEA* PLANT NAMED 'MEDITATION'**

(50) Latin Name: ***Echinacea purpurea*×*Echinacea tennesseensis***
Varietal Denomination: Meditation

(71) Applicant: Marco van Noort, Warmond (NL)

(72) Inventor: Marco van Noort, Warmond (NL)

(73) Assignee: Marco Van Noort Breeding BV, Warmond (NL)

( * ) Notice: Subject to any disclaimer, the term of this patent is extended or adjusted under 35 U.S.C. 154(b) by 181 days.

(21) Appl. No.: 13/815,990

(22) Filed: Mar. 20, 2013

(65) Prior Publication Data

US 2013/0219578 P1 Aug. 22, 2013

(51) Int. Cl.
*A01H 5/02* (2006.01)

(52) U.S. Cl.
CPC ..... *A01H 5/025* (2013.01)
USPC ..... Plt./428

(58) Field of Classification Search
CPC ..... A01H 5/025; A01H 5/00; A01H 5/02
USPC ..... Plt./428
See application file for complete search history.

(56) References Cited

PUBLICATIONS

Upov Pluto Plant Variety Database 20141030, retrieved on Nov. 5, 2014, retrieved from the Internet at <www3.wipo.int/pluto/user/en/index.jsp>.*

* cited by examiner

*Primary Examiner* — June Hwu
(74) *Attorney, Agent, or Firm* — Penny J. Aguirre

(57) ABSTRACT

A new cultivar of hybrid *Echinacea*, 'Meditation', characterized by its short plant height, its bushy plant habit, its floriferous habit, and its inflorescences that are long lasting with a single to semi-double row of ray florets that are bright pink in color surrounding red cones.

2 Drawing Sheets

Botanical classification: *Echinacea purpurea*×*Echinacea tennesseensis*.
Variety denomination: 'Meditation'.

BACKGROUND OF THE INVENTION

The present Invention relates to a new and distinct cultivar of *Echinacea purpurea* and will be referred to hereafter by its cultivar name, 'Meditation'. 'Meditation' represents a new coneflower, an herbaceous perennial grown for landscape use.

The new cultivar arose from an ongoing breeding program conducted by the Inventor in a designated field at his nursery in Warmond, The Netherlands. The goal of his breeding program is to create new cultivars of *Echinacea* that exhibit a short and firm plant habit combined with inflorescences with attractive form and coloration. The Inventor made a cross in summer of 2006 between unnamed proprietary plants of *Echinacea purpurea*×*Echinacea tennesseensis* from his breeding line. 'Meditiation' was selected by the Inventor as a single unique plant amongst the resulting seedlings from the above cross in July of 2008.

Asexual propagation of the new cultivar was first accomplished by in vitro propagation under the direction of the Inventor in Rijswijk, The Netherlands in April of 2010 by the Inventor. Asexual propagation by in vitro propagation has determined that the be stable and are reproduced true to type in successive generations.

SUMMARY OF THE INVENTION

The following traits have been repeatedly observed and represent the characteristics of the new cultivar. These attributes in combination distinguish 'Meditation' as a unique cultivar of *Echinacea*.

1. 'Meditation' exhibits a short plant habit.
2. 'Meditation' exhibits a bushy plant habit.
3. 'Meditation' is very floriferous; producing many flowering stems.
4. 'Meditation' exhibits flowers that are long lasting.
5. 'Meditation' exhibits inflorescences with a single to semi-double row of ray florets that are bright pink in color surrounding red cones.

Both the female parent and male parent differ from 'Meditation' in being taller in height, in having less bushy plant habits, and in producing many less flowering stems. 'Meditation' can be most closely compared to the cultivars 'Little Magnus' (U.S. Plant Pat. No. 15,973) and 'CBG Cone 2' (U.S. Plant Pat. No. 18,546). Both are similar to 'Meditation' in having short plant heights. 'Little Magnus' differs from 'Meditation' in having inflorescences with ray florets that are darker in color. 'CBG Cone 2' differs from 'Meditation' in having inflorescences with ray florets that are shorter and thinner and held more horizontally and in having cones that are more yellow-brown in color.

BRIEF DESCRIPTION OF THE DRAWING

The accompanying photographs depict two year-old plants of 'Meditation' as field grown outdoors in Warmond, The Netherlands.

The photograph in FIG. 1 provides a view of numerous plants in bloom.

Figure 1:
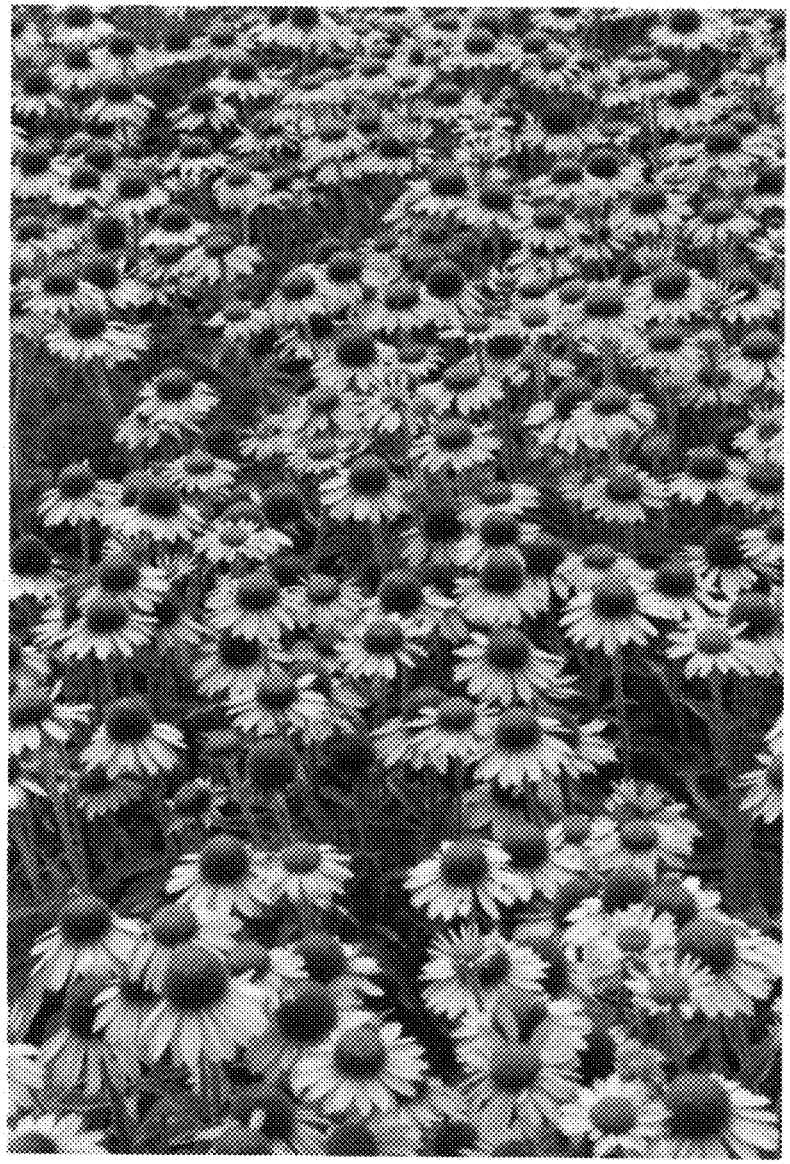
Figure 2:
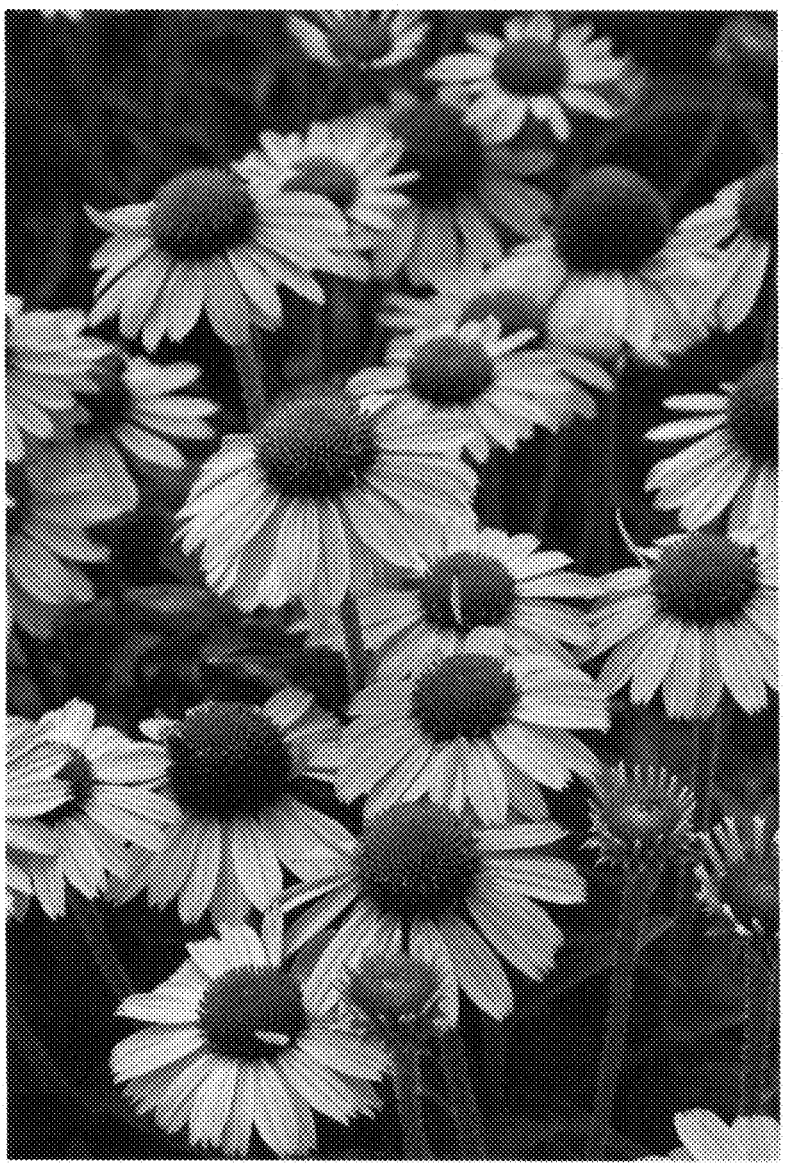

The photograph in FIG. 2 shows a close-up of inflorescences of 'Meditation'.

The colors in the photographs may differ slightly from the color values cited in the detailed botanical description, which accurately describe the colors of the new *Echinacea*.

BOTANICAL DESCRIPTION OF THE PLANT

The following is a detailed description of one-year-old plants of the new cultivar as grown outdoors in a field in Warmond, The Netherlands. The plants were grown under average day temperatures of 10° to 25° C. and average night temperatures of 3° to 15° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Continuously from early July to mid-October in The Netherlands.

*Plant habit*.—Herbaceous perennial, clump forming, broad upright.

*Height and spread*.—Reaches about 33 cm in height 28 cm in spread.

*Hardiness*.—U.S.D.A. Zones 3 to 4.

*Diseases resistance*.—Not more susceptible to pests/diseases than other *Echinacea* varieties.

*Root description*.—Fibrous.

*Propagation*.—Tissue culture preferred.

*Growth rate*.—Low to moderately vigorous.

Stem description:

*Shape*.—Rounded.

*Stem color*.—144A.

*Stem size*.—An average of 6 mm in diameter and 16.8 cm in length (excluding inflorescence).

*Stem strength*.—Very strong.

*Stem aspect*.—Stems grow in an average angle of 75°.

*Stem surface*.—Moderately rough to touch and densely covered with very short strigose hairs about 1 mm in length and NN155D in color.

*Stem number*.—Average of 3 main stems.

*Internode length*.—Average of 2.7 cm in length.

*Branching* .—Main flowering stem grows from base.

Foliage description:

*Leaf shape*.—Narrow ovate, carinate.

*Leaf division*.—Simple.

*Leaf base*.—Attenuate.

*Leaf apex*.—Acute.

*Leaf venation*.—Pinnate, color: upper surface; 146C to 146D, lower surface; 146C.

*Leaf margins*.—Entire, slightly undulate.

*Leaf attachment*.—Petiolate.

*Leaf arrangement*.—Alternate.

*Leaf size*.—Average of 8.9 cm in length and 2.9 cm in width.

*Leaf color*.—Young upper surface; 137A to 137B, young lower surface; between 137D and 138A, mature upper surface; N137A to N137B, mature lower surface; 137C.

*Leaf surface*.—Upper and lower surfaces are dull and densely covered with short strigose hairs about 0.5 mm in length and 155C in color.

*Petioles*.—V-shaped, 1.8 cm in length and shorter towards the top of the stem, average diameter is 3 mm, upper surface 145A to 145B in color, lower surface 145A in color, both surfaces glossy and covered with short strigose hairs, average length is 0.3 mm and 155C in color.

Flower description:

*Type*.—Terminal capitulum.

*Capitulum number*.—An average of 3 per stem.

*Lastingness of inflorescence*.—About 2 weeks.

*Capitulum size*.—Matures to about 5.9 cm in height and 6.8 cm in diameter, disk is about 3.6 cm in diameter.

*Fragrance*.—Faint, sweet fragrance.

*Involucral bracts or phyllary*.—About 60 arranged in 3 overlapping rows, average of 9 mm in length and 3 mm in width, cuneate base, acute apex, entire margin, narrow ovate in shape and curved towards the peduncle, upper surface; N137A to N137B in color, lower surface; 137B in color, upper surface is smooth, lower surface is smooth and with margins moderately covered with very short strigose hairs average length of 0.3 mm and 157D in color.

*Buds*.—Flattened globular in shape, immature ray florets near vertical (upright), an average of 2.7 cm in length and 3.3 cm in diameter, color; 174B to 174C, center is between 143A and 146A.

*Peduncle*.—Strong, terminal is an average of 11.5 cm in length and 4 mm in diameter, terminals held upright with secondary and tertiary peduncles held at an average angle of 30° to vertical, color; 144A, surface is slightly glossy and moderately covered with short strigose hairs about 0.8 mm in length and NN155D in color.

*Ray florets*.—Rotate, single to semi-double, average of 15 per inflorescence (average of 11 when single and 18 when semi-double), obovate to narrow obovate in shape, upper and lower surfaces smooth, ribbed lengthways and very slightly glossy, about 3.5 cm in length and 1.3 cm in width, emarginated to praemorse apex, cuneate base, entire margin, slightly drooping in an average angle of about 35° downward from horizontal, color of upper surface when opening; 63B, color of lower surface when opening; 51C to 51D, margins 59D, color of upper surface when fully open; a blend of 63C and 64D, tip is 64A, color of lower surface when fully open; 181D, margins 58D, upper surface fading to 68C to 68D to 186C to 186D, lower surface fading to 186C, heavily tinged 148D.

*Disk flowers* (*bisexual*).—Numerous, about 320, arranged spirally on disc, apex is acute and upper 9% is free, fused (tubular) base, entire margin (upper 9%), lower 91% fused into a tube, average of 1.1 cm in length and 3 mm in width, upper surface and lower surface are smooth and glossy, color: when opening upper and lower surface; ranging between 145C to 150C to 150D, tip 145A to 145B, when fully opened upper and lower surface; 181A to 181B, tinged 153D.

*Disk spines*.—Average of 320, acicular in shape, acute apex, attenuate base, smooth and glossy surface, color is 53A at apex, 25B to 25C in mid region and 145A to 145B at base.

*Receptacle*.—Ovate in shape, an average of 1.7 cm in height and 1.1 cm in diameter, and 157D in color.

Reproductive organs (present on disk florets only):

*Gynoecium*.—Pistil; 1, 6 mm in length, style; about 4 mm in length and 150D in color, stigma is decurrent and 187A in color, ovary; 157A to 157B in color.

*Androcoecium*.—Stamens; 5, filaments; 4 mm in length and 145C to 145D in color, anthers; basifixed in shape, about 3 mm in length and N200A in color, pollen is moderate in quantity and 17A to 17B in color.

*Fruit/seed*.—No seed production has been observed.

It is claimed:

1. A new and distinct cultivar of *Echinacea* plant named 'Meditation' substantially as herein illustrated and described.

* * * * *